United States Patent [19]

Schrading

[11] 3,968,799

[45] July 13, 1976

[54] PREFOLDED DISPOSABLE DIAPER

[75] Inventor: Mark S. Schrading, Neenah, Wis.

[73] Assignee: Kimberly-Clark Corporation, Neenah, Wis.

[22] Filed: Apr. 4, 1975

[21] Appl. No.: 565,046

[52] U.S. Cl. ............................... 128/287; 128/284
[51] Int. Cl.² ......................................... A61F 13/16
[58] Field of Search ............................. 128/284, 287

[56] References Cited
UNITED STATES PATENTS

| | | | |
|---|---|---|---|
| 3,196,874 | 7/1965 | Hrubecky | 128/287 |
| 3,710,797 | 1/1973 | Marsan | 128/284 |
| 3,724,464 | 4/1973 | Enloe | 128/284 |
| 3,774,610 | 11/1973 | Eckert | 128/287 |
| 3,848,595 | 11/1974 | Endres | 128/284 |
| 3,860,004 | 1/1975 | Nystrand | 128/287 |

*Primary Examiner*—Aldrich F. Medbery
*Attorney, Agent, or Firm*—Daniel J. Hanlon, Jr.; William D. Herrick; Raymond J. Miller

[57] ABSTRACT

A prefolded disposable diaper which is originally of substantially rectangular configuration and which is folded transversely in half with the body contacting surface internally disposed and has the outer segments of the transverse fold inverted and tucked back into the interior of the folded diaper to form a pair of facing triangular panels on each side of the folded diaper to define a centrally disposed flat-bottomed pocket. The internally disposed surfaces of the facing panels on each side of the pocket are adhesively attached to the interior body contacting surface by means of a strategically placed, narrow stripe of adhesive spaced outwardly from the pocket and disposed perpendicular to and straddling the transverse fold. When the diaper of this construction is opened up and partially flattened by the user in preparing the diaper for application to the child, the strategic placement of the adhesive stripes causes the side edges of the diaper to automatically flare outward. Then, when the child is placed on the opened diaper in the usual manner, and the diaper ends are pulled around the child's waist, these flared-out side edges will press against the thighs and provide a contoured fit while the adhesive attachment stripes maintain the central depending pocket in the crotch area.

3 Claims, 6 Drawing Figures

PREFOLDED DISPOSABLE DIAPER

BACKGROUND OF THE INVENTION

Most disposable diapers now being marketed are prefolded in various ways as a convenience to the user in providing a better fit when the diaper is applied to the child. These folds are generally designed to minimize leakage at the inner thigh area as well as to provide a centrally depending pocket to more effectively contain excrement. Exemplary of one such style is the diaper described in Hrubecky U.S. Pat. No. 3,196,874 of July 27, 1965 in which multiple diagonally disposed infolds and outfolds provide a prefolded diaper of generally triangular shape which is contoured to provide a centrally disposed depending pocket and leg-hugging side edges. While this prefolded diaper serves its intended purpose well, attempts have been made to provide a diaper with somewhat similar contour but with less complicated folds in order to simplify fabrication.

A simplified diaper structure of this type is described in Eckert et al. U.S. Pat. 3,774,610 of Nov. 27, 1973. In that diaper, the pair of diagonal outfolds on each side of the diaper is eliminated, and the centrally disposed pocket is maintained by adhesively attaching facing surface portions of the triangular pocket panels to each other. This diaper also functions well in use, but as set forth in the patent, it is necessary for the user to manually turn down the side edges of the diaper when applying it to the child in order to provide the desired snug fit at the thighs.

The present invention is directed to a structure which utilizes the simpler fold similar to that described in Eckert et al but in addition provides an improved adhesive attachment means for the pocket panels. The improved attachment means is placed on the inner contacting faces of the folded pocket in such a manner that when the diaper is opened up preparatory to placing the child on it, the attachment means will operate to automatically flare out the side edges of the diaper into a position which will assure that these side edges will press against the thighs as the diaper is fastened to the child without requiring extra manipulation of the side edges as set forth in the prior art.

The above features and other advantages of the invention will become apparent by reference to the following specification and accompanying drawings.

BRIEF DESCRIPTION OF THE DRAWINGS

In the drawings in which like numerals indicate like elements.

DETAILED DESCRIPTION OF THE PREFERRED EMBODIMENTS

It is understood that, with respect to its basic structural elements, the diaper itself is of the usual construction now in common use in disposable diapers, i.e., an absorbent core comprising a batt of absorbent fibers interposed between a fluid-pervious cover of nonwoven material or the like on the body contacting side and a fluid-impervious backing sheet of thin plastic film or the like. Disposable diapers presently on the market range in size from about 10 inches × 14 inches for newborns to about 14 inches × 18 inches for ambulatory infants. It is also understood that the diaper may be provided with pressure sensitive tapes for fastening purposes. Accordingly, no detailed description of such elements is included herein because, in themselves, they are not critical to the invention.

Figure 1:
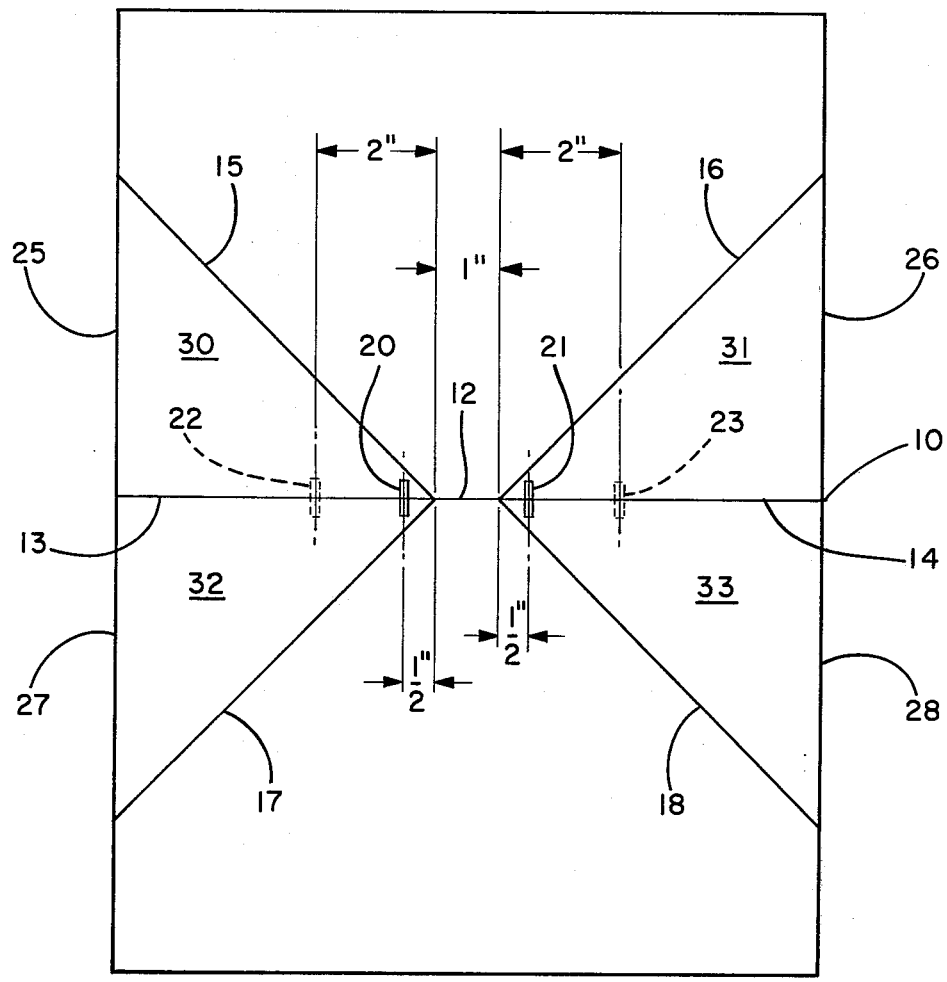
FIG. 1 is a plan view of the body contacting or inner surface of a diaper prior to folding and indicating the location of fold lines and adhesive means which secure contacting face portions of the diaper together in accordance with this invention.

The plan view of FIG. 1 is intended to show the body contacting surface of the diaper prior to folding and to indicate the location of the fold lines, as well as the location and disposition of the adhesive means which is used to secure contacting faces of the folded diaper to each other in accordance with the invention.

Figure 2:
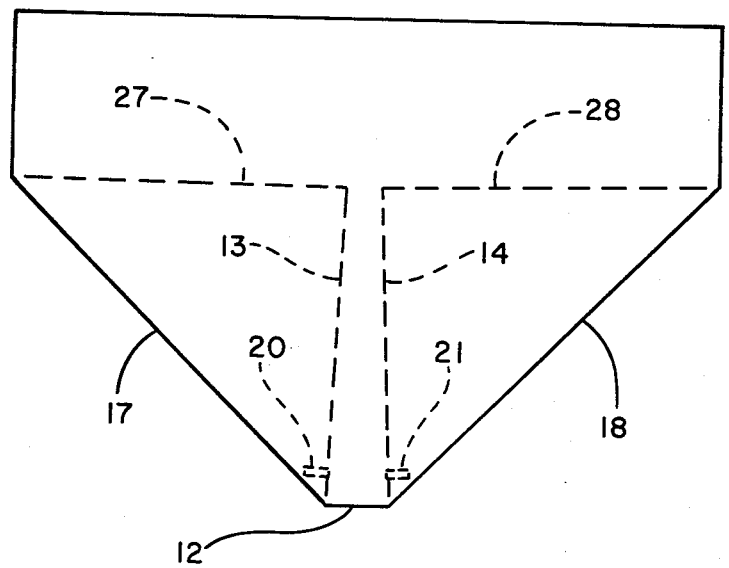
FIG. 2 is a plan view of the diaper of FIG. 1 in its folded condition.

Reference numeral 10 indicates the medial transverse line on which the diaper is folded. This line is divided into a central portion 12 which defines the bottom of a centrally disposed pocket in the folded diaper, and two outboard segments 13 and 14, which define inward tucks and cooperate along with diagonal fold lines 15, 16, 17 and 18 to form the complete pocket in the folded diaper shown in FIG. 2.

Reference numerals 20 and 21 illustrate narrow stripes of adhesive which straddle lines 13 and 14 respectively and serve to secure each face of triangular panels 30 and 32, and of triangular panels 31 and 33 to the respective body contacting surface of the folded diaper respectively in the small adhesive areas indicated at 20 and 21.

Phantom numerals 22 and 23 illustrate an alternate location of such adhesive stripes.

Figure 3:
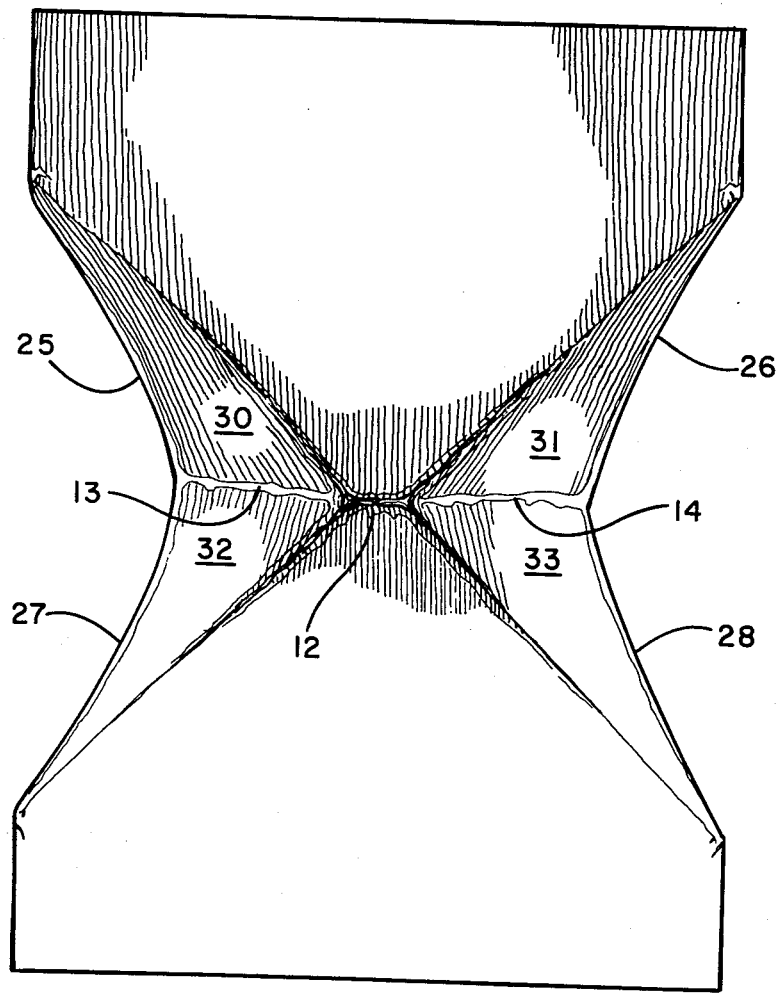
FIG. 3 is a plan view of the body contacting surface of the FIG. 2 diaper after it has been opened up and is ready for placing the child on it in the diapering process.

In FIG. 1, the central segment 12 of fold line 10 defining the bottom of the central pocket is shown as being 1 inch long and adhesive strips 20 and 21, which straddle fold line 10's two outboard segments 13 and 14 respectively are disposed one half inch outwardly from the points where the central segment 12 of fold line 10 is intersected by diagonal fold lines 15, 17 and 16, 18 which extend from central segment 12. Alternate locations for similar adhesive stripes 22 and 23 illustrated as phantom lines in the drawings, are shown as being disposed about 2 inches from their respective intersections with central segment 12 of fold line 10. The length of the adhesive stripe itself is not critical, but stripes of from 1 inch to 2 inches have been found effective for the purposes described herein. The adhesive itself should be of any of the known types which are pliable when set, form a permanent bond with the substrates, are non-irritating and dermatologically safe. Hot melt, aqueous emulsion, or solvent system adhesives can be used. FIG. 3 illustrates the appearance of the diaper of FIG. 2 after it has been spread open by the user preparatory to placing the child on it in the diapering process. As will be noted here, merely opening the folded diaper at the ends and flattening it out causes side edges 25, 27 and 26, 28 to flare out away from their folded, tucked in position so that when the child is placed on the open diaper these side edges will automatically press into snug contact with the thighs as the diaper ends are pulled up around the waist and fastened to complete the diapering process. The user is required to use no additional manipulation of the diaper to achieve this result. When the adhesive stripes 20, 21 or 22, 23 are strategically located as illustrated in the drawings they serve as hinge areas which exert forces on the triangular panels to which they are attached in such manner that the diaper side edges fan out in the convenient position indicated.

Figure 4:
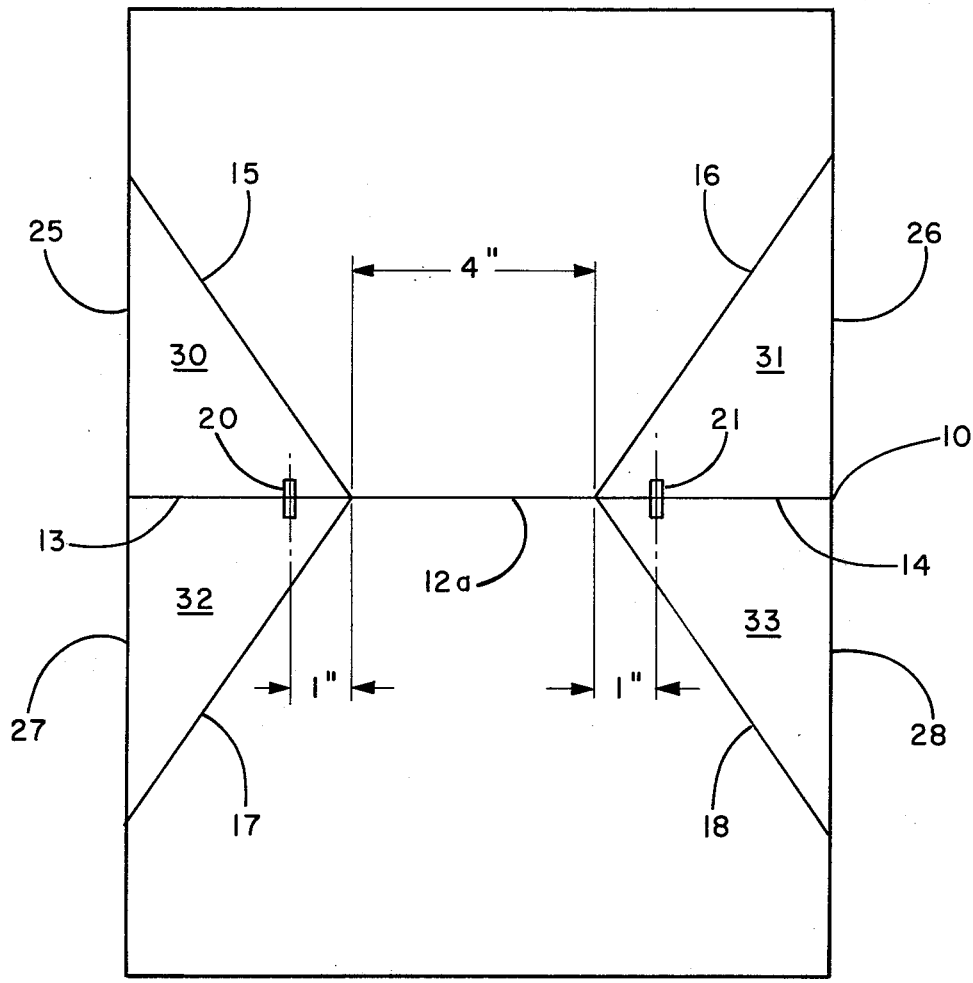
FIG. 4 is a plan view similar to FIG. 1 showing another embodiment of the diaper.
Figure 5:
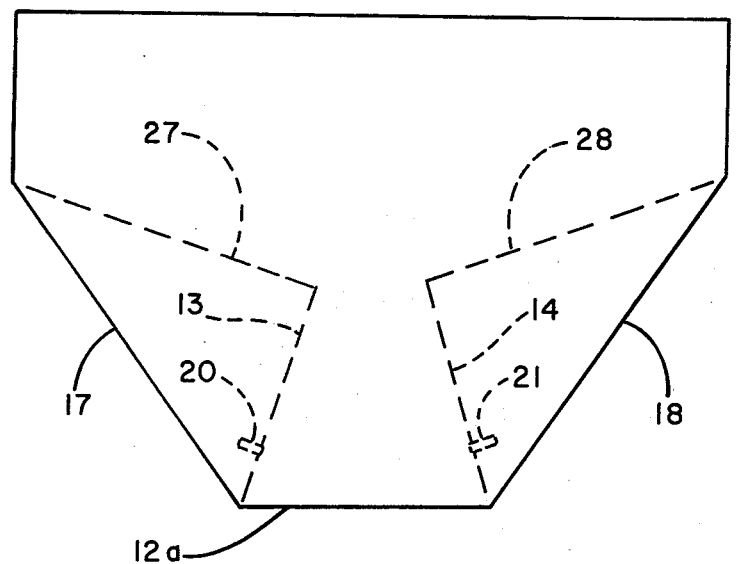
FIG. 5 is a plan view of the diaper of FIG. 4 in its folded condition.
Figure 6:
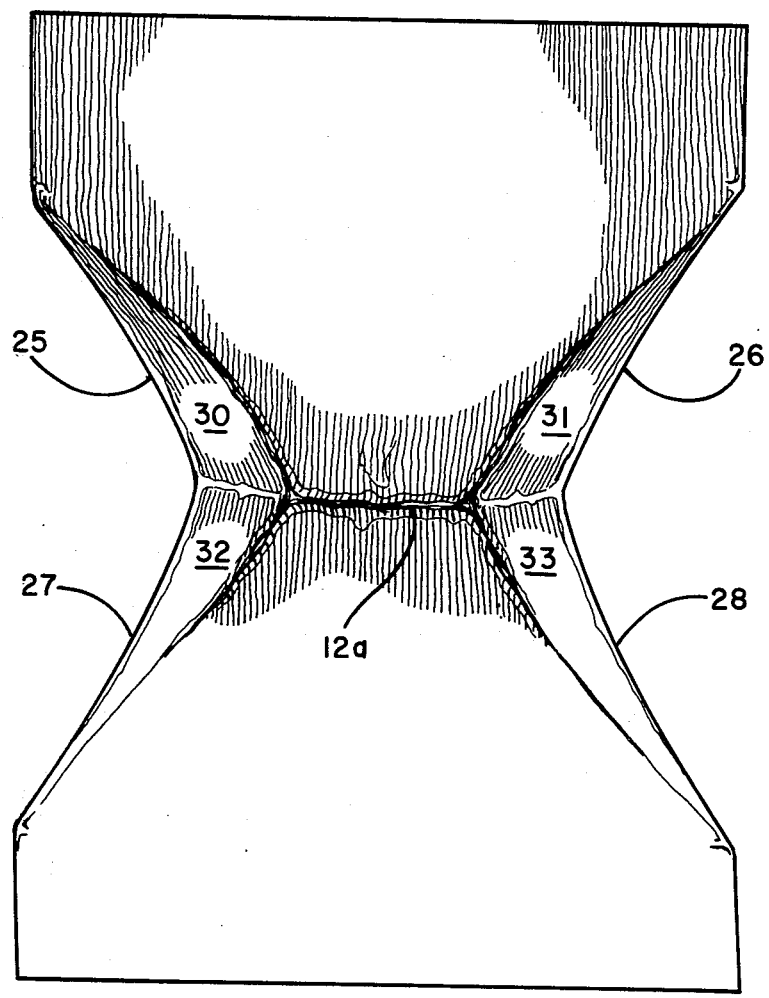
FIG. 6 is a plan view of the FIG. 4 diaper after it has been opened up in preparation for the diapering process.

FIGS. 4, 5 and 6 show the invention in slightly modified form. These figures are substantially the same as FIGS. 1, 2, 3 except that the central segment 12a of fold line 10 defining the bottom of the central pocket is about 4 inches long and the adhesive stripes 20 and 21 are disposed about 1 inch from the intersection where the end points of central segment 12a meet the respective diagonal folds radiating outward therefrom.

What is claimed:

1. In a prefolded disposable diaper of substantially rectangular configuration having an exterior surface and an interior body contacting surface which is folded in half transversely with the body contacting surface internally disposed and in which outer segments of the transverse fold are inverted and tucked back into the interior of the diaper to form a pair of facing triangular panels on each side of the folded diaper to define a central disposed flat-bottomed pocket, the improvement wherein the internally disposed surfaces of the facing panels on each side of the pocket are adhesively attached to the interior body contacting surface by means of a short narrow stripe of adhesive spaced outwardly from the pocket and disposed perpendicular to and straddling the inverted transverse fold, the flat bottom of said diaper having a dimension of about 1 inch to 4 inches and each of said adhesive stripes being spaced from the respective end portion of said pocket a distance of from about ½ inch to 2 inches.

2. The diaper of claim 1 wherein said pocket is 1 inch wide and each of said stripes is spaced about one half inch from the respective end of said pocket.

3. The diaper of claim 1 wherein said pocket is 4 inches wide and each of said stripes is spaced about 1 inch from the respective pocket ends.

* * * * *